(12) United States Patent
Alemi

(10) Patent No.: US 9,117,173 B2
(45) Date of Patent: Aug. 25, 2015

(54) SYSTEMS AND METHODS OF PREDICTING A SUBJECT'S MEDICAL OUTCOME

(75) Inventor: Farrokh Alemi, McLean, VA (US)

(73) Assignee: Georgetown University, Washington, DC (US)

( * ) Notice: Subject to any disclaimer, the term of this patent is extended or adjusted under 35 U.S.C. 154(b) by 162 days.

(21) Appl. No.: 13/701,816

(22) PCT Filed: Jun. 6, 2011

(86) PCT No.: PCT/US2011/039316
§ 371 (c)(1),
(2), (4) Date: Dec. 3, 2012

(87) PCT Pub. No.: WO2011/153543
PCT Pub. Date: Dec. 8, 2011

(65) Prior Publication Data
US 2013/0085980 A1 Apr. 4, 2013

Related U.S. Application Data

(60) Provisional application No. 61/351,749, filed on Jun. 4, 2010.

(51) Int. Cl.
| | | |
|---|---|---|
| G06N 5/02 | (2006.01) | |
| G06F 19/24 | (2011.01) | |
| G06F 19/00 | (2011.01) | |
| G06Q 10/00 | (2012.01) | |
| G06Q 50/22 | (2012.01) | |

(52) U.S. Cl.
CPC ............. *G06N 5/022* (2013.01); *G06F 19/24* (2013.01); *G06F 19/34* (2013.01); *G06Q 10/00* (2013.01); *G06Q 50/22* (2013.01)

(58) Field of Classification Search
None
See application file for complete search history.

(56) References Cited

U.S. PATENT DOCUMENTS

| | | | |
|---|---|---|---|
| 6,278,464 B1 * | 8/2001 | Kohavi et al. | 345/440 |
| 6,978,244 B2 | 12/2005 | Rovinelli et al. | |
| 2002/0082868 A1 | 6/2002 | Pories et al. | |
| 2003/0220777 A1 * | 11/2003 | Kitchen et al. | 703/11 |
| 2006/0129324 A1 * | 6/2006 | Rabinoff et al. | 702/19 |
| 2008/0154514 A1 | 6/2008 | Magness et al. | |
| 2009/0132460 A1 | 5/2009 | Alemi | |

OTHER PUBLICATIONS

Weisenberger, D.J. et al. "CpG island methylator phenotype underlies sporadic microsatellite instability and is tightly associated with BRAF mutation in colorectal cancer." Nature genetics 38.7 (2006): 787-793. doi:10.1038/ng1834.*

Wang, Y. et al. "Induction of model trees for predicting continuous classes." Working Paper Series ISSN 1170-487X. Working Paper 96/23. Oct. 1996.*

(Continued)

*Primary Examiner* — Jeffrey A Gaffin
*Assistant Examiner* — Benjamin Buss
(74) *Attorney, Agent, or Firm* — Klarquist Sparkman, LLP

(57) ABSTRACT

Disclosed are methods of constructing systems for predicting a subject's medical outcome. Also disclosed are methods and systems for predicting a subject's medical outcome. The disclosed methods and systems can include identifying a group of subjects with the same medical condition and classifying this group of subjects into one or more subgroups. The subgroups are classified based on similarity of medical outcome, using classification and regression trees (CART) to generate a classification tree based on the presence of identifying genetic characteristics. Each node in the classification tree describes the presence of a specific genetic marker and each branch in the classification tree describes a genetic profile that predicts a subject's medical outcome.

9 Claims, 7 Drawing Sheets

(56) References Cited

OTHER PUBLICATIONS

Friedman, J. et al. "Additive logistic regression: a statistical view of boosting (with discussion and a rejoinder by the authors)." The annals of statistics 28.2 (2000): 337-407.*

Hahn, T. et al. "Integrating Neurobiological Markers of Depression" Arch Gen Psychiatry. 2011;68(4):361-368. Published online Dec. 6, 2010. doi:10.1001/archgenpsychiatry.2010.178.*

Knable MB, et al. "Molecular abnormalities in the major psychiatric illnesses: classification and regression tree (CRT) analysis of post-mortem prefrontal markers." Mol Psychiatry 2002;7:392-404. DOI: 10.1038/sj.mp.4001034.*

International Search Report and Written Opinion issued Nov. 18, 2011, by the Korean Intellectual Property Office, for corresponding PCT patent application No. PCT/US2011/039316, 11 pp.

* cited by examiner

SYSTEMS AND METHODS OF PREDICTING A SUBJECT'S MEDICAL OUTCOME

CROSS REFERENCE TO RELATED APPLICATIONS

This is the U.S. National Stage of International Application No. PCT/US2011/039316, filed Jun. 6, 2011, which was published in English under PCT Article 21(2), which in turn claims the benefit of U.S. Provisional Application No. 61/351,749, filed Jun. 4, 2010. The provisional application is incorporated herein by reference in its entirety.

FIELD OF THE DISCLOSURE

This disclosure relates to the field of individualized medicine, specifically to systems and methods of predicting a subject's response to treatment and in particular, to antidepressants, such as citalopram.

BACKGROUND

Personalized medicine is built on the notion that there is an inherent contradiction of going from studies of groups of patients to advice and recommendations for an individual patient. It involves tools and statistics to help clinicians advise one patient at a time, even in contradiction to results of group studies. A great part of these tools and statistics involve the genetic profile of the patient and other information (e.g., co-morbidity, concurrent medication, allergies), which can be used to tailor diagnoses and treatments based on patients' unique characteristics.

Yet, it is generally difficult to deduce from population/group studies what will work for an individual patient. Some medication may work for some patients, but not for others. A multitude of factors may account for any variation in medical effects. Examples include the type of medication, dosage, absorption rate, severity of illness, drug-drug interactions, allelic combination of a patient's genes encoding detoxification enzymes, age, nutritional status, and co-morbidities. Given the complexity of determining the right medication for patients, health providers need a tool for providing more effective prescriptions beyond the trial and error methods.

SUMMARY

Disclosed are methods of constructing systems for predicting a subject's medical outcome. The disclosed methods include identifying a group of subjects with the same medical condition and classifying this group of subjects into one or more subgroups. The subgroups are classified based on similarity of medical outcome, using classification and regression trees (CART) to generate a classification tree based on the presence of identifying genetic characteristics. Each node in the classification tree describes the presence of a specific genetic marker and each branch in the classification tree describes a genetic profile that predicts a subject's medical outcome.

Also disclosed are methods for predicting a subject's medical outcome. In such methods a subject is identified that has a specific medical condition or at risk of acquiring a medical condition. The subject's medical outcome is predicted by comparing the subject's genetic profile with a set of control genetic profiles, wherein the control genetic profiles are generated from a group of subjects with the same disease using classification and regression trees (CART) based on the presence of identifying genetic characteristics. By matching a subject's genetic profile to a branch in the classification tree the subject's medical outcome is predicted.

Systems are also disclosed for predicting a subject's medical outcome. Such systems typically include a computer or more than one computers that has been specifically programmed to classify a group of subjects identified with the same disease into one or more subgroups. The one or more subgroups are classified based on similarity of medical outcome, using classification and regression trees (CART) to generate a classification tree based on the presence of identifying genetic characteristics and wherein each node in the classification tree describes the presence of a specific genetic marker and each branch in the classification tree describes a genetic profile that predicts a subject's medical outcome.

Disclosed are methods for predicting a subject's response to an antidepressant, such as citalopram. Such methods include obtaining a sample for a subject. The samples is then tested to detect at least one single nucleotide polymorphism (SNP), wherein the at least one SNP is rs7238368 or rs809736 in nucleolar protein 4 (NOL4), rs10499638 in RAR-related orphan receptor A isoform a (RORA), rs2697992 in retinoblastoma protein-binding zinc finger (PRDM2), rs6127921 in bone morphogenetic protein 7 precursor (BMP7) or rs6046805 in open reading frame C20orf26. Detection of at least one SNP predicts a subject's responsiveness to the antidepressant.

The foregoing and other features and advantages of the disclosure will become more apparent from the following detailed description of a several embodiments which proceeds with reference to the accompanying figures.

DETAILED DESCRIPTION OF SEVERAL EMBODIMENTS

I. Summary of Terms

Figure 1:
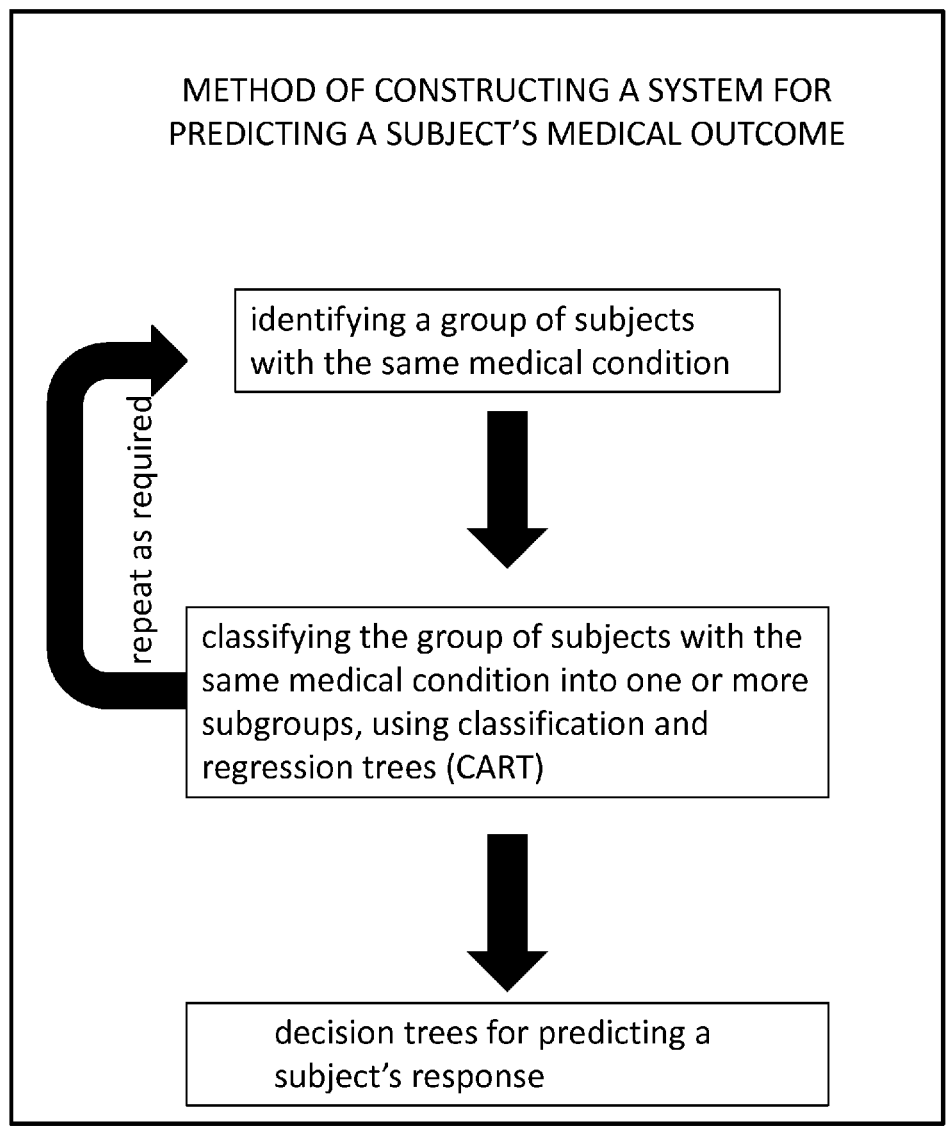
FIG. 1 shows a diagram of instructions for the construction of a system for predicting medical outcomes.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting To facilitate review of the various embodiments of this disclosure, the following explanations of specific terms are provided:

Administration: To provide or give a subject an agent, such as a composition that targets depression in a subject, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Allele: A particular form of a genetic locus, distinguished from other forms by its particular nucleotide sequence, or one of the alternative polymorphisms found at a polymorphic site.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see European patent publication No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

Array: An arrangement of molecules, such as biological macromolecules (such as polypeptides or nucleic acids) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from a few (such as three) to at least six, at least 20, at least 25, or more. In particular examples, an array includes nucleic acid molecules, such as oligonucleotide sequences that are at least 15 nucleotides in length, such as about 15-40 nucleotides in length, such as at least 18 nucleotides in length, at least 21 nucleotides in length, or even at least 25 nucleotides in length. In one example, the molecule includes oligonucleotides attached to the array via their 5'- or 3'-end.

Within an array, each arrayed sample is addressable, in that its location can be reliably and consistently determined within the at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Citalopram: An antidepressant medication which affects neurotransmitters. Citalopram's mechanism of action is believed to be preventing the uptake of serotonin by nerve cells after it has been released. Since uptake is an important mechanism for removing released neurotransmitters and terminating their actions on adjacent nerves, the reduced uptake caused by citalopram results in more free serotonin in the brain to stimulate nerve cells. Citalopram is sold under numerous brand names including Celexa and Cipramil. Citalopram is in the class of drugs called selective serotonin reuptake inhibitors (SSRIs), a class that also contains fluoxetine (Prozac), paroxetine (Paxil) and sertraline (Zoloft).

Classification and Regression Trees (CART): A nonparametric data-driven tree-based analysis that produces either classification or regression trees, depending on whether the dependent variable is categorical or numeric, respectively. Decision trees are formed by a collection of rules based on variables in the modeling data set. Rules based on variables' values are selected to get the best split to differentiate observations based on the dependent variable. Once a rule is selected and splits a node into two, the same process is applied to each "child" node (e.g., it is a recursive procedure). Splitting stops when CART detects no further gain can be made, or some pre-set stopping rules are met. (Alternatively, the data is split as much as possible and then the tree is later pruned.) Each branch of the tree ends in a terminal node. Each observation falls into one and exactly one terminal node, and each terminal node is uniquely defined by a set of rules.

Correlation: A correlation between a phenotypic trait, such as response to a pharmaceutical agent, and the presence or absence of a genetic marker (or haplotype or genotype) can be observed by measuring the phenotypic trait and comparing it to data showing the presence or absence of one or more genetic markers. Some correlations are stronger than others, meaning that in some instances subjects with a specific phenotypic trait will display a particular genetic marker (i.e., 100% correlation). In other examples the correlation will not be as strong, meaning that a subject with specific phenotypic trait will only display a particular genetic marker 90%, 85%, 70%, 60%, 55%, or 50% of the time. In some instances, a haplotype which contains information relating to the presence or absence of multiple markers can also be correlated to a specific phenotypic trait. Correlations can be described using various statistical analyses.

Diagnostic: Identifying the presence or nature of a pathologic condition, such as, but not limited to a condition treatable by medication, for example the identification of a subjects predisposition to treatment, or lack thereof, for depression with a specific pharmaceutical agent. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition.

Disease or Medical Condition: Any condition that causes or has a negative effect on a person's health, as determined by a physician, pharmacist, dentist, clinician, or as identified by a set of health/health-related codes. Examples of health/health-related codes include, but are not limited to, the International Classification of Diseases (ICD) (such as ICD, Ninth Revision, (ICD-9)/ICD, Ninth Revision, Clinical Modification (ICD-9-CM)), Healthcare Common Procedure Coding System (HCPCS), Current Procedural Terminology (CPT), National Drug Code (NDC), and the like.

Effective amount: An amount of agent, that is sufficient to generate a desired response, such as reduce or eliminate a sign or symptom of a condition or disease. When administered to a subject, a dosage will generally be used that will achieve target tissue concentrations In some examples, an "effective amount" is one that treats (including prophylaxis) one or more symptoms and/or underlying causes of any of a disorder or disease.

Genetic predisposition: Susceptibility of a subject to s therapy, for example a subject's response to a pharmaceutical agent, for example an anti-depression therapeutic. Detecting a genetic predisposition includes detecting the presence of the disease itself, such as but not limited to an early stage of the disease process. Detecting a genetic predisposition also includes detecting the risk of developing the disease, and determining the susceptibility of that subject to developing the disease or to having a poor prognosis for the disease. Thus, if a subject has a genetic predisposition to a disease process they do not necessarily develop the disease.

Genomic target sequence: A sequence of nucleotides located in a particular region in the human genome that corresponds to one or more specific genetic abnormalities, such as a nucleotide polymorphism, a deletion, an insertion, or an amplification. The target can be for instance a coding sequence; it can also be the non-coding strand that corresponds to a coding sequence. The target can also be a non-coding sequence, such as intronic sequence. In several examples, genomic target sequences are genomic sequences of genes that encode nucleolar protein 4 (NOL4), RAR-related orphan receptor A isoform a (RORA), retinoblastoma protein-binding zinc finger (PRDM2), bone morphogenetic protein 7 precursor (BMP7), C20orf26.

Gene: A segment of DNA that contains the coding sequence for a protein, wherein the segment may include promoters, exons, introns, and other untranslated regions that control expression.

Genotype: An unphased 5' to 3' sequence of nucleotide pair(s) found at a set of one or more polymorphic sites in a locus on a pair of homologous chromosomes in an individual. "Genotyping" is a process for determining a genotype of an individual.

Gini impurity: A measure of how often a randomly chosen element from the set would be incorrectly labeled if it were randomly labeled according to the distribution of labels in the subset. Gini impurity is used in the CART algorithm. Gini impurity is can be computed by summing the probability of each item being chosen times the probability of a mistake in categorizing that item. It reaches its minimum (zero) when all cases in the node fall into a single target category. To compute Gini impurity for a set of items, suppose y takes on values in $\{1, 2, \ldots, m\}$, and let $f_i$=the fraction of items labeled with value i in the set.

$$I_G(f) = \sum_{i=1}^m f_i(1-f_i) = \sum_{i=1}^m (f_i - f_i^2) = \sum_{i=1}^m f_i - \sum_{i=1}^m f_i^2 = 1 - \sum_{i=1}^m f_i^2$$

Haplotype: A 5' to 3' sequence of nucleotides found at a set of one or more polymorphic sites in a locus on a single chromosome from a single individual. "Haplotype pair" is the two haplotypes found for a locus in a single individual. With regard to a population, haplotypes are the ordered, linear combination of polymorphisms (e.g., single nucleotide polymorphisms, SNPs) in the sequence of each form of a gene (on individual chromosomes) that exists in the population. "Haplotyping" is a process for determining one or more haplotypes in an individual and includes use of family pedigrees, molecular techniques and/or statistical inference. "Haplotype data" is the information concerning one or more of the following for a specific gene: a listing of the haplotype pairs in an individual or in each individual in a population; a listing of the different haplotypes in a population; frequency of each haplotype in that or other populations, and any known associations between one or more haplotypes and a trait.

Haplotype block: Sites of closely located SNPs which are inherited in blocks. A haplotype block includes a group of SNP locations that do not appear to recombine independently and that can be grouped together. Regions corresponding to blocks have a few common haplotypes which account for a large proportion of chromosomes. Identification of haplotype blocks is a way of examining the extent of linkage disequilibrium (LD) in the genome. The "Hap-Map" project (see the internet at the Hap-Map website) describes the mapping of haplotype blocks in the human genome.

There are programs to available on the internet for the identification of haplotype blocks, such as program HAPBLOCK™ which runs on both PC and Unix and is available from the USC website on the internet. A further program, which in addition to block identification also has visualization and selection of "tagging" SNPs is HAPLOBLOCK-FINDER™, which runs interactively on the web or can be downloaded for local machine use (Unix or PC). It can be accessed at the program website available on the internet.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a specific genetic locus, so it specifically hybridizes with a mutant allele (and not the wild-type allele) or so that it specifically hybridizes with a wild-type allele (and not the mutant allele).

"Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization. In one example, an oligonucleotide is specifically hybridizable to DNA or RNA nucleic acid sequences including an allele of a gene, wherein it will not hybridize to nucleic acid sequences containing a polymorphism.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following is an exemplary set of hybridization conditions and is not limiting:

Very High Stringency (detects sequences that share at least 90% identity)
    Hybridization: 5×SSC at 65° C. for 16 hours
    Wash twice: 2×SSC at room temperature (RT) for 15 minutes each
    Wash twice: 0.5×SSC at 65° C. for 20 minutes each
High Stringency (detects sequences that share at least 80% identity)
    Hybridization: 5×-6×SSC at 65° C.-70° C. for 16-20 hours
    Wash twice: 2×SSC at RT for 5-20 minutes each
    Wash twice: 1×SSC at 55° C.-70° C. for 30 minutes each
Low Stringency (detects sequences that share at least 50% identity)
    Hybridization: 6×SSC at RT to 55° C. for 16-20 hours
    Wash at least twice: 2×-3×SSC at RT to 55° C. for 20-30 minutes each Inhibiting or treating a disease: Inhibiting the full development of a disease or condition, for example, in a subject who is at risk for a disease such as depression. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Locus: A location on a chromosome or DNA molecule corresponding to a gene or a physical or phenotypic feature, where physical features include polymorphic sites.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

In several examples, oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 70 bases, for example about 10-25 bases, such as 12, 15 or 20 bases.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: A variation in a gene sequence. The polymorphisms can be those variations (DNA sequence differences) which are generally found between individuals or different ethnic groups and geographic locations which, while having a different sequence, produce functionally equivalent gene products. The term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Further, the term is also used interchangeably with allele as appropriate.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

A "single nucleotide polymorphism (SNP)" is a single base (nucleotide) difference in a DNA sequence among individuals in a population. A tag SNP is a representative single nucleotide polymorphism (SNP) in a region of the genome with high linkage disequilibrium (the non-random association of alleles at two or more loci) that is associated with a disease, such as ALS. A tag SNP can be used to identify other SNPs, such as those with a specified $r^2$ value from the tag SNP, which are associated with a disease, such as ALS. Statistical methods to identify a tag SNP are known (see Hoperin et al., Bioinformatics 21 (suppl): i195-i203, 2005, herein incorporated by reference).

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Sample: A sample, such as a biological sample, is a sample obtained from a subject. As used herein, biological samples include all clinical samples useful for detection of depression in subjects, including, but not limited to, cells, tissues, and bodily fluids, such as: blood; derivatives and fractions of blood, such as serum. In a particular example, a sample includes blood obtained from a human subject, such as whole blood or serum.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only.

Single Nucleotide Polymorphism (SNP): A DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case we say that there are two alleles: C and T. Almost all common SNPs have only two alleles. Within a population, SNPs can be assigned a minor allele frequency—the lowest allele frequency at a locus that is observed in a particular population. This is simply the lesser of the two allele frequencies for single-nucleotide polymorphisms. There are variations between human populations, so a SNP allele that is common in one geographical or ethnic group may be much rarer in another. SNPs can be used in personalized medicine. Herein, SNPs are used to predict a subject's medical outcome.

Subject: Living multi-cellular vertebrate organisms, a category that includes human and non-human mammals (such as laboratory or veterinary subjects).

II. Overview of Several Embodiments

When it comes to personalized medicine, it is important to change current methods so that it reflects the new constraints that would work for one patient. Hence, what is needed is a simplified and accurate prediction model that does not rely on selecting various models to foresee a potential medical outcome. Also, what is needed is a strategy that detects whether a particular medication works for the patient at hand—independent of whether it works for others or for an average patient.

No single gene has predicted a large percent of patients' response to citalopram, a common antidepressant. As disclosed herein, the inventors examined the combination of various genetic markers within sub-group of patients to see if response to citalopram could be accurately predicted. Data available through the Sequenced Treatment Alternatives to Relieve Depression (STAR*D) database were used in the reported studies. Three boosted Classification and Regression Trees (CART) were created to identify 16 subgroups of patients, among whom one could predict positive or negative response to citalopram was significantly different from 0.5 (p-value≤0.1). In 10 fold cross-validation, this ensemble of trees made no predictions in 33% of cases but in the remaining 67% of cases it accurately predicted response to citalopram in 78% of cases. These data show that, even though not every case can be predicted, for the majority of the patients, genetic markers can be used to guide selection of citalopram.

Citalopram (brand names Celexa, Cipramil, etc.) is a common antidepressant prescribed in United States and many other markets. Worldwide, more than 18 million patients have taken this medication but the majority of patients (60%) do not achieve remission of their depression symptoms. Untreated or poorly treated depression leads to significant functional impairment and may even lead to self-medication through alcohol and illicit drugs and sometimes suicide. Poorly treated or untreated patients are 2 times more likely to be hospitalized and incur 19 times greater cost than patients with properly managed depression. One way out of these grim statistics is to anticipate response to citalopram and prescribe it for patients that are likely to benefit from it. Since it may take weeks to determine if an antidepressant will be helpful, it would be useful to know in advance if a particular medication is likely to be successful for a given patient.

The search for genetic markers for response to antidepressants has identified a number of markers. Variants in certain genes, such as HTR2A, GRIK4, KCNK2, FKBP5, PDE11A and BDNF and SLC6A4, have been identified in some but not all studies to be predictive of response to antidepressants. Despite progress, the effect size is small and the percentage of outcomes correctly predicted from any single genetic marker is near random chance. This has led some investigators to conclude that there is "limited clinical utility in matching antidepressants to patient's genetic profile." The studies to date have not examined the combination of various genetic markers or examined sub-group of patients among whom response might be predicted more accurately. Herein the inventors demonstrated the utility of predicting response to citalopram from a combination of genetic markers within subgroups of patients.

Subgroup analysis can be used in order to examine response to antidepressants among different groups. Looking at racial subgroups is one way to do so. One can also group patients by age, by co-morbidity, by type of depression and by a host of different factors including certain genes. In fact, any one of the genes in a patient profile can be used to define a new subgroup. If there are "n" predictors of response to therapy, there are 2n possible subgroups. This raises the possibility of a very large number of subgroups, too many to be practical. Not surprisingly, none of the studies reported to date have done a complete subgroup analysis. One way to limit the number of sub-groups examined is to examine only those groups within which an accurate prediction can be made. Herein a Classification and Regression Trees (CART) procedure to identify subgroups of patients among whom an accurate prediction can be made.

As disclosed herein CART is used to group cases; when a new patient presents, the group corresponding to the patient is identified and used to guide the patient. This approach allows one to select a small subset of data and predict a patient's response from the experience of cases within that subset. Contrary to usual statistical procedures, the objective is not to rely on a large data set but on the smallest most relevant subset of data.

A. Methods of Predicting Response to Treatment

Disclosed are methods of constructing systems for predicting a subject's medical outcome. An exemplary diagram of the method is presented as FIG. 1 The disclosed methods include identifying a group of subjects with the same medical condition and classifying this group of subjects into one or more subgroups. The subgroups are classified based on similarity of medical outcome, using classification and regression trees (CART) to generate a classification tree based on the presence of identifying genetic characteristics. Each node in the classification tree describes the presence of a specific genetic marker and each branch in the classification tree describes a genetic profile that predicts a subject's medical outcome.

Figure 2:
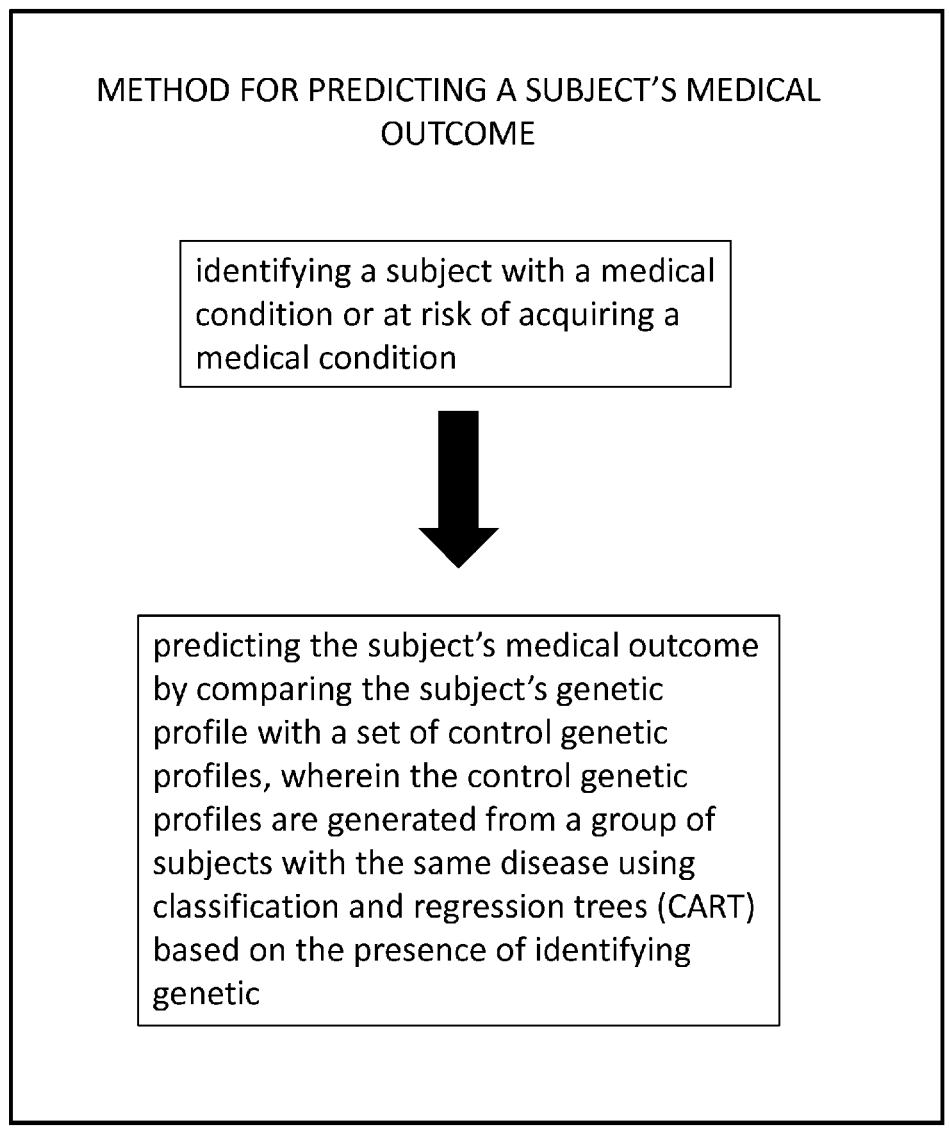
FIG. 2 shows a diagram of instructions for the method of predicting medical outcomes.

Also disclosed are methods for predicting a subject's medical outcome. An exemplary diagram of the method is presented as FIG. 2. Such methods include identifying a subject that has a specific medical condition or at risk of acquiring a medical condition. The subject's medical outcome is predicted by comparing the subject's genetic profile with a set of control genetic profiles, wherein the control genetic profiles are generated from a group of subjects with the same disease using classification and regression trees (CART) based on the presence of identifying genetic characteristics. By matching a subject's genetic profile to a branch in the classification tree the subject's medical outcome is predicted.

Figure 3:
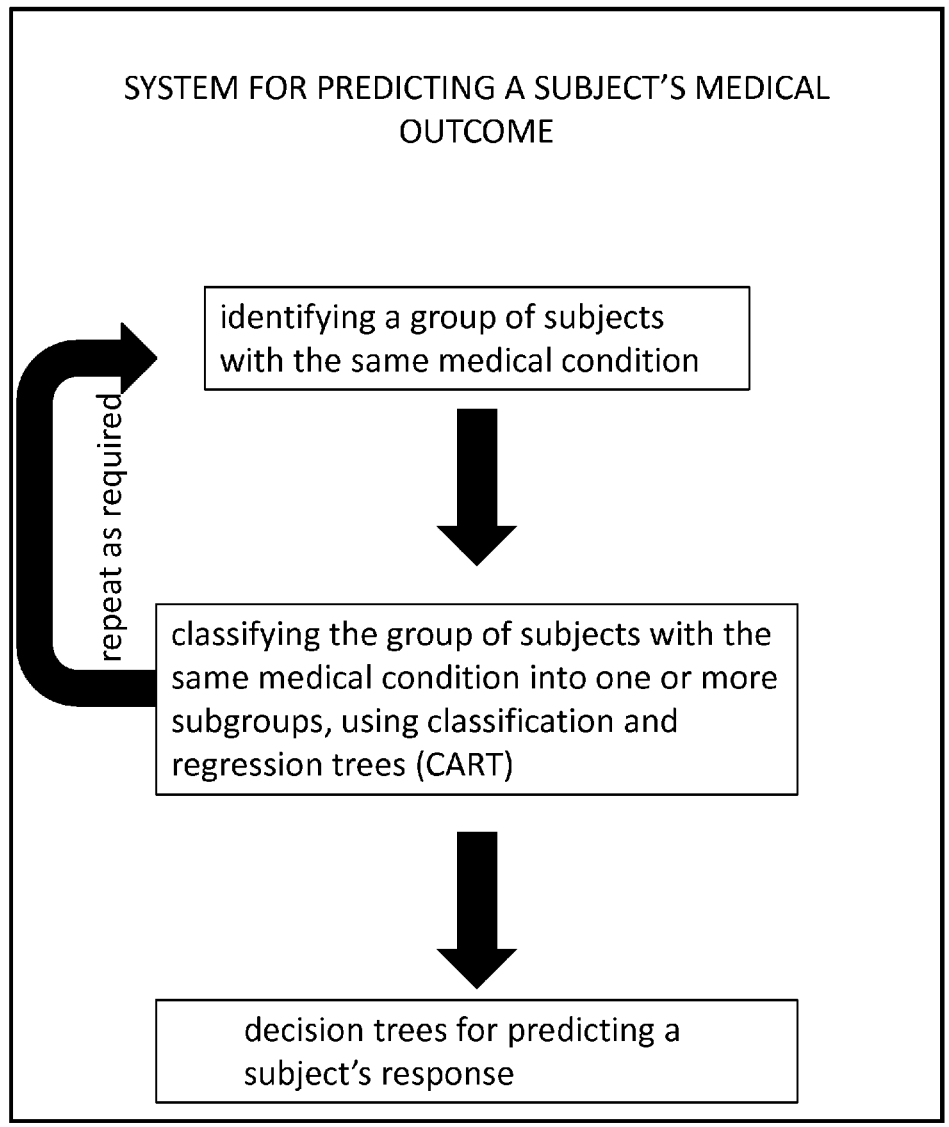
FIG. 3 shows a diagram of a system for predicting medical outcomes.

Systems are also disclosed for predicting a subject's medical outcome. An exemplary diagram of the system is presented as FIG. 3. Such systems typically include a computer or more than one computers that has been specifically programmed to classify a group of subjects identified with the same disease into one or more subgroups. The one or more subgroups are classified based on similarity of medical outcome, using classification and regression trees (CART) to generate a classification tree based on the presence of identifying genetic characteristics and wherein each node in the classification tree describes the presence of a specific genetic marker and each branch in the classification tree describes a genetic profile that predicts a subject's medical outcome.

In some embodiments of the disclosed methods and systems performing CART includes a 10 fold cross-validation and pruning factor of 1 to all unclassified cases to classify the subgroups into the branches of a tree. In some embodiments of the disclosed methods and systems CART is halted if none of the subgroups identified have a probability of positive or negative response significantly different from 0.05 (p-value≤0.10). In some embodiments of the disclosed methods and systems CART is boosted. In some embodiments of the disclosed methods and systems the method or system predicts medical outcome with at least about 65% accuracy, such as at least 65% accuracy, at least 67% accuracy, at least 69% accuracy, at least 70% accuracy, at least 75% accuracy, at least 80% accuracy, at least 85% accuracy, at least 90% accuracy, at least 95% accuracy, including 65% to 70% accuracy, 80% to 84% accuracy 85% to 90% accuracy, including 65% accuracy, 66% accuracy, 67% accuracy, 68% accuracy, 69% accuracy, 70% accuracy, 71% accuracy, 72% accuracy, 73% accuracy, 74% accuracy, 75% accuracy, 76% accuracy, 77% accuracy, 78% accuracy, 79% accuracy, 80% accuracy, 81% accuracy, 82% accuracy, 83% accuracy, 84% accuracy, 85% accuracy, 86% accuracy, 87% accuracy, 88% accuracy, 89% accuracy, 90% accuracy, 91% accuracy, 92% accuracy, 93% accuracy, 94% accuracy, 95% accuracy, 96%, 97% or greater.

In some embodiments of the disclosed methods and systems, CART includes removing the statistically insignificant subgroups and repeating the analysis. In such a situation, each time a set of cases are taken out, the analysis repeats and creates new classes. Each class is then tested. If any class is still not significant, then the cases are taken out. The process continues until all classified cases lead to significant subgroups and all unclassified cases lead to insignificant subgroups.

In some examples, the medical outcome is a disease progression, including indication of patient survival. In other examples, the medical outcome is response to medical treatment, such as but not limited to administration of a therapeutic agent. In specific examples, a therapeutic agent is an antidepressant, such as a selective serotonin reuptake inhibitor (e.g., citalopram).

Identification of subjects with the same medical condition can be accomplished by selecting all patients with the same diagnosis within electronic health records (EHR). EHRs are simply individual health records in a digitized format that can be accessed via a computer or computer-based system over a network. EHRs are designed to keep information about each encounter with the patient. When the patient shows again, the information form the previous visits can be retrieved. For example, EHRs may include a person's health characteristics, medical history, past and current diagnoses, lab reports and results, x-rays, photographs, prescribed medication, billing and insurance information, contact information, demographics, and the like.

Information recorded in EHRs can be used for a multitude of reasons in addition to being stored for future retrieval. For instance, they can be used to benchmark clinical practices, set pay for performance incentives, identify trends in illness in a community, and measure quality of care.

Additionally, EHRs can provide a remarkable advantage for analysis. Non-limiting benefits include providing access to data on a large number of patients, organizing terms in a standardized manner (e.g., ICD-9, ICD-9-CM, etc.), and allowing data on an entire population to be available so as to avoid sampling.

EHRs may be used to select an individual's characteristics. Those selected may be based upon their uniqueness to the individual. Alternatively, they may be different from an average patient in the practice.

Nonlimiting examples of characteristics include race, gender, age, symptoms, side effects, allergies, dietary habits, physical and/or mental condition(s), genetic traits, genetic signatures, haplotypes, specific polymorphisms, such as single nucleotide polymorphisms and the like. It is expected that some characteristics may overlap or be partially redundant when compared to other individuals. For example, it is well known that any person who lists being pregnant as a characteristic is also a female.

In some embodiments of the disclosed systems and methods, the identifying genetic characteristics are the presence of one or more single nucleotide polymorphisms (SNPs). In specific examples, the SNPs includes at least one of rs7238368 or rs809736 in nucleolar protein 4 (NOL4), rs10499638 in RAR-related orphan receptor A isoform a (RORA) rs2697992 in retinoblastoma protein-binding zinc finger (PRDM2), rs6127921 in bone morphogenetic protein 7 precursor (BMP7), rs6046805 in open reading frame C20orf26 or a combination thereof.

Disclosed are methods for predicting a subject's response to an antidepressant, such as citalopram. Such methods include obtaining a sample for a subject. The samples is then tested to detect at least one single nucleotide polymorphism (SNP), wherein the at least one SNP is rs7238368 or rs809736 in nucleolar protein 4 (NOL4), rs10499638 in RAR-related orphan receptor A isoform a (RORA), rs2697992 in retinoblastoma protein-binding zinc finger (PRDM2), rs6127921 in bone morphogenetic protein 7 precursor (BMP7) or rs6046805 in open reading frame C20orf26. Detection of at least one SNP predicts a subject's responsiveness to the antidepressant. In some examples, at least one SNP comprising rs7238368 or rs809736 in nucleolar protein 4 (NOL4), rs10499638 in RAR-related orphan receptor A isoform a (RORA) or a combination thereof is detected. Detection of the at least one SNP indicates that the subject will not be responsive to the antidepressant. In some examples at least one of rs7238368 and rs809736 in nucleolar protein 4 (NOL4) and rs10499638 in RAR-related orphan receptor A isoform a (RORA) is detected. Detection of rs7238368 and rs809736 in NOL4 and rs10499638 in RORA indicates the subject has an at least 80% likelihood of not being responsive to the antidepressant, such as a 81%, 82%, 83%, 84%, 85%, 86%, 87%, 88%, 89%, 90%, 91%, 92%, 93%, 94% or greater likelihood. In some examples, detection of rs7238368 and rs809736 in NOL4 and rs10499638 in RORA indicates the subject has an about 89% likelihood of not being responsive to the antidepressant.

In some examples, at least one SNP is rs2697992 in retinoblastoma protein-binding zinc finger (PRDM2), rs6127921 in bone morphogenetic protein 7 precursor (BMP7), rs6046805 in open reading frame C20orf26 or a combination thereof is detected. Detection of the at least one SNP indicates that the subject will be responsive to the antidepressant. In some examples, detecting rs2697992 in retinoblastoma protein-binding zinc finger (PRDM2), rs6127921 in bone morphogenetic protein 7 precursor (BMP7) and rs6046805 in open reading frame C20orf26 indicates the subject has an at least 60% likelihood of being responsive to the antidepressant, such as at least 61%, 62%, 63%, 64%, 65%, 66%, 67%, 68%, 69%, 70%, 71%, 72%, 73%, 74%, 75%, 76%, 77% or greater likelihood. In some examples detection of rs2697992 in retinoblastoma protein-binding zinc finger (PRDM2), rs6127921 in bone morphogenetic protein 7 precursor (BMP7) and rs6046805 in open reading frame C20orf26 indicates the subject will be responsive to the antidepressant with a 65% probability.

With regard to the SNPs, the SNPs are identified by name. The exact sequence of the SNP can be determined from the database of SNPs available at the NCBI website (Entrez SNP, dbSNP build 128). The "position" is the location in the genome of the SNP, referring to the nucleotide position from the p-terminus of the chromosome in the human genome, see the NCBI SNP website, available on the interne.

Once a patient's predicted response to citalopram is determined, an indication of that response can be displayed and/or conveyed to a clinician or other caregiver. For example, the indication can be displayed on a computer display or printed on a tangible medium (e.g., paper) that can be perceived by the clinician for consideration by the clinician. In some embodiments, the indication can comprise a numerical value that is representative of the patient's determined response to citalopram, or the indication can be a qualitative indication of response (such as one or more of yes/no/possibly or a graphical or schematic indication of probable response to the drug).

Additional or alternative steps can include one or more of the following depending on the patient's determined response to citalopram: a) prescribing a dosage of citalopram for the patient if the patient's determined response to citalopram is considered to be positive; b) not prescribing a dosage of citalopram for the patient if the patient's determined response to citalopram is considered to be negative; c) administering a dosage of citalopram to the patient if the patient's determined response to citalopram is considered to be positive; d) not administering a dosage of citalopram to the patient if the patient's determined response to citalopram is considered to be negative; and e) adjusting a particular dosage of citalopram for prescription or administration to the patient based on the patient's determined response to citalopram. In an alternative embodiment, the method can include recommending one or more of the steps a)-e).

B. Molecular Methods

The methods disclosed herein can involve an assessment of nucleic acid sequence, for example to detect the presence of genetic signatures that can predict a subject's response to a pharmaceutical agent, such as an antidepressant including citalopram.

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

When the nucleic acid of interest is present in a cell, it can be necessary to first prepare an extract of the cell and then perform further steps, such as differential precipitation, column chromatography, extraction with organic solvents and the like, in order to obtain a sufficiently pure preparation of nucleic acid. Extracts can be prepared using standard techniques in the art, for example, by chemical or mechanical lysis of the cell. Extracts then can be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. When chaotropic salts are used, it can be desirable to remove the salts from the nucleic acid-containing sample. This can be accomplished using standard techniques in the art such as precipitation, filtration, size exclusion chromatography and the like.

In some instances, messenger RNA can be extracted from cells. Techniques and material for this purpose are known to those skilled in the art and can involve the use of oligo dT attached to a solid support such as a bead or plastic surface. In some embodiments, the mRNA can be reversed transcribed into cDNA using, for example, a reverse transcriptase enzyme. Suitable enzymes are commercially available from, for example, Invitrogen, Carlsbad Calif. Optionally, cDNA prepared from mRNA can also be amplified.

Optionally, the nucleic acid samples obtained from the subject are amplified prior to detection. Target nucleic acids are amplified to obtain amplification products, including sequences from a SNP, can be amplified from the sample prior to detection. Typically, DNA sequences are amplified, although in some instances RNA sequences can be amplified or converted into cDNA, such as by using RT PCR.

In specific examples, the target sequences to be amplified from the subject include one or different SNP, or a nucleotide sequence of interest including the SNP.

A pair of primers can be utilized in the amplification reaction. One or both of the primers can be labeled, for example with a detectable radiolabel, fluorophore, or biotin molecule. The pair of primers includes an upstream primer (which binds 5' to the downstream primer) and a downstream primer (which binds 3' to the upstream primer). The pair of primers used in the amplification reactions are selective primers which permit amplification of a size related marker locus. Primers can be selected to amplify a SNP, or a nucleic acid including a SNP. Numerous primers can be designed by those of skill in the art simply by determining the sequence of the desired target region, for example, using well known computer assisted algorithms that select primers within desired parameters suitable for annealing and amplification.

If desired, an additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

The nucleic acids obtained from the sample can be genotyped to identify the particular allele present for a marker locus. A sample of sufficient quantity to permit direct detection of marker alleles from the sample can be obtained from the subject. Alternatively, a smaller sample is obtained from the subject and the nucleic acids are amplified prior to detection. Any target nucleic that is informative for a chromosome haplotype can be detected. Generally, the target nucleic acid corresponds to a SNP described above, or an SNP described above. Any method of detecting a nucleic acid molecule can be used, such as hybridization and/or sequencing assays.

Nucleic acid molecules corresponding to a SNP can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Hybridization conditions for a given combination of array and target material can be optimized routinely in an empirical manner close to the $T_m$ of the expected duplexes, thereby maximizing the discriminating power of the method. For example, the hybridization conditions can be selected to permit discrimination between matched and mismatched oligonucleotides. Hybridization conditions can be chosen to correspond to those known to be suitable in standard procedures for hybridization to filters (and optionally for hybridization to arrays). In particular, temperature is controlled to substantially eliminate formation of duplexes between sequences other than an exactly complementary allele of the selected marker. A variety of known hybridization solvents can be employed, the choice being dependent on considerations known to one of skill in the art (see U.S. Pat. No. 5,981,185).

Once the target nucleic acid molecules have been hybridized with the labeled probes, the presence of the hybridization complex can be analyzed, for example by detecting the complexes.

Methods for detecting hybridized nucleic acid complexes are well known in the art. In one example, detection includes detecting one or more labels present on the oligonucleotides, the target (e.g., amplified) sequences, or both. Detection can include treating the hybridized complex with a buffer and/or a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when radiolabels are used. In particular examples, the method further includes quantification, for instance by determining the amount of hybridization.

Allele-specific PCR differentiates between target regions differing in the presence of absence of a variation or polymorphism. PCR amplification primers are chosen based upon their complementarity to the target sequence, such as nucleic acid sequence in an SNP, or a haplotype block including a tag SNP, a specified region of an allele including a tag SNP, or to the tag SNP itself. The primers bind only to certain alleles of the target sequence. This method is described by Gibbs, *Nucleic Acid Res.* 17:12427 2448, 1989, herein incorporated by reference.

Further screening methods employ the allele-specific oligonucleotide (ASO) screening methods (e.g. see Saiki et al., *Nature* 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the wildtype allele (haplotype block).

Ligase can also be used to detect point mutations, such as the SNPs disclosed herein, in a ligation amplification reaction (e.g. as described in Wu et al., *Genomics* 4:560-569, 1989). The ligation amplification reaction (LAR) utilizes amplification of specific DNA sequence using sequential rounds of template dependent ligation (e.g. as described in Wu, supra, and Barany, *Proc. Nat. Acad. Sci.* 88:189-193, 1990).

Amplification products generated using the polymerase chain reaction can be analyzed by the use of denaturing gradient gel electrophoresis. Different alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

Differentiation between alleles (haplotype blocks) based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527, 1986, and Myers et al., in Genomic Analysis, A Practical Approach, K. Davies Ed. IRL Press Limited, Oxford, pp. 95 139, 1988. The electrophoresis system is maintained at a temperature slightly below the Tm of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with high $T_m$'s.

Generally, the target region is amplified by polymerase chain reaction. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions. DNA fragments differing by a single base change will migrate through the gel to different positions, which can be visualized by ethidium bromide staining.

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Target sequences, such as alleles or haplotype blocks can be differentiated using single-strand conformation polymorphism analysis, which identifies base differences by alteration in electrophoretic migration of single stranded PCR products, for example as described in Orita et al., *Proc. Nat. Acad. Sci.* 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles or haplotype blocks.

Differences between target sequences, such as alleles or haplotype blocks, can also be detected by differential chemical cleavage of mismatched base pairs, for example as described in Grompe et al., *Am. J. Hum. Genet.* 48:212-222, 1991. In another method, differences between target sequences, such as alleles or haplotype blocks, can be detected by enzymatic cleavage of mismatched base pairs, as described in Nelson et al., Nature Genetics 4:11-18, 1993. Briefly, genetic material from an animal and an affected family member can be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms.

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}P$ or $^{35}S$. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a nucleic acid sequence wherein a polymorphism is present that is associated with ALS, such as a tag SNP, and thus defining a genetic marker, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Exemplary tandem repeat hybridization probes for use in the methods disclosed are those that recognize a small number of fragments at a specific locus at high stringency hybridization conditions, or that recognize a larger number of fragments at that locus when the stringency conditions are lowered.

In particular examples involving genotyping of multiple marker loci, the methods can be performed using an array that includes a plurality of markers. Such arrays can include nucleic acid molecules. In one example, the array includes nucleic acid oligonucleotide probes that can hybridize to one or more alleles.

Arrays can be used to detect the presence of amplified sequences including one or more SNPs or tag SNPs of interest using specific oligonucleotide probes. In one example, a set of oligonucleotide probes is attached to the surface of a solid support for use in detection of marker alleles that define haplotypes. Additionally, if an internal control nucleic acid sequence was amplified in the amplification reaction (see above), an oligonucleotide probe can be included to detect the presence of this amplified nucleic acid molecule. The oligonucleotide probes bound to the array can specifically bind sequences amplified in the amplification reaction (such as under high stringency conditions).

The methods and apparatus in accordance with the present disclosure takes advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes can be substantially reduced.

The length of each oligonucleotide sequence employed in the array can be selected to optimize binding to a specific allele of a marker locus associated with depression. An optimum length for use with a particular marker nucleic acid sequence under specific screening conditions can be determined empirically. Thus, the length for each individual element of the set of oligonucleotide sequences included in the array can be optimized for screening. In one example, oligonucleotide probes are from about 20 to about 35 nucleotides in length or about 25 to about 40 nucleotides in length.

The oligonucleotide probe sequences forming the array can be directly linked to the support, for example via the 5'- or 3'-end of the probe. In one example, the oligonucleotides are bound to the solid support by the 5' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support. Alternatively, the oligonucleotide probes can be attached to the support by sequences such as oligonucleotides or other molecules that serve as spacers or linkers to the solid support.

In particular examples, the array is a microarray formed from glass (silicon dioxide). Suitable silicon dioxide types for the solid support include, but are not limited to: aluminosilicate, borosilicate, silica, soda lime, zinc titania and fused silica (for example see Schena, *Micraoarray Analysis*. John Wiley & Sons, Inc, Hoboken, N.J., 2003). The attachment of nucleic acids to the surface of the glass can be achieved by methods known in the art, for example by surface treatments that form from an organic polymer. Particular examples include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567), organosilane compounds that provide chemically active amine or aldehyde groups, epoxy or polylysine treatment of the microarray. Another example of a solid support surface is polypropylene.

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the surface treatment is amine-containing silane derivatives. Attachment of nucleic acids to an amine surface occurs via interactions between negatively charged phosphate groups on the DNA backbone and positively charged amino groups (Schena, Micraoarray Analysis. John Wiley & Sons, Inc, Hoboken, N.J., 2003). In another example, reactive aldehyde groups are used as surface treatment. Attachment to the aldehyde surface is achieved by the addition of 5'-amine group or amino linker to the DNA of interest. Binding occurs when the nonbonding electron pair on the amine linker acts as a nucleophile that attacks the electropositive carbon atom of the aldehyde group.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Biaxially oriented polypropylene (BOPP) films are also suitable in this regard; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as see PCT Publication No. WO 85/01051 and PCT Publication No. WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

In particular examples, the oligonucleotide probes on the array include one or more labels, which permit detection of oligonucleotide probe:target sequence hybridization complexes.

C. Computer Implemented Methods and Media

The methods and systems disclosed herein can be implemented on a computer, for example a specifically programmed computer. Thus, disclosed are computers or tangible computer readable medium with instructions for the disclose methods. Tangible computer readable medium means any physical object or computer element that can store and/or execute computer instructions. Examples of tangible computer readable medium include, but not limited to, a compact disc (CD), digital versatile disc (DVD), blu-ray disc (BD), usb floppy drive, floppy disk, random access memory (RAM), read-only memory (ROM), erasable programmable read-only memory (EPROM), optical fiber, and the like. It should be noted that the tangible computer readable medium may even be paper or other suitable medium in which the instructions can be electronically captured, such as optical scanning. Where optical scanning occurs, the instructions may be compiled, interpreted, or otherwise processed in a suitable manner, if necessary, and then stored in computer memory.

Alternatively, it may be a plugin or part of a software code that can be included in, or downloaded and installed into a computer application. As a plugin, it may be embeddable in any kind of computer document, such as a webpage, word document, pdf file, mp3 file, etc.

Figure 6:
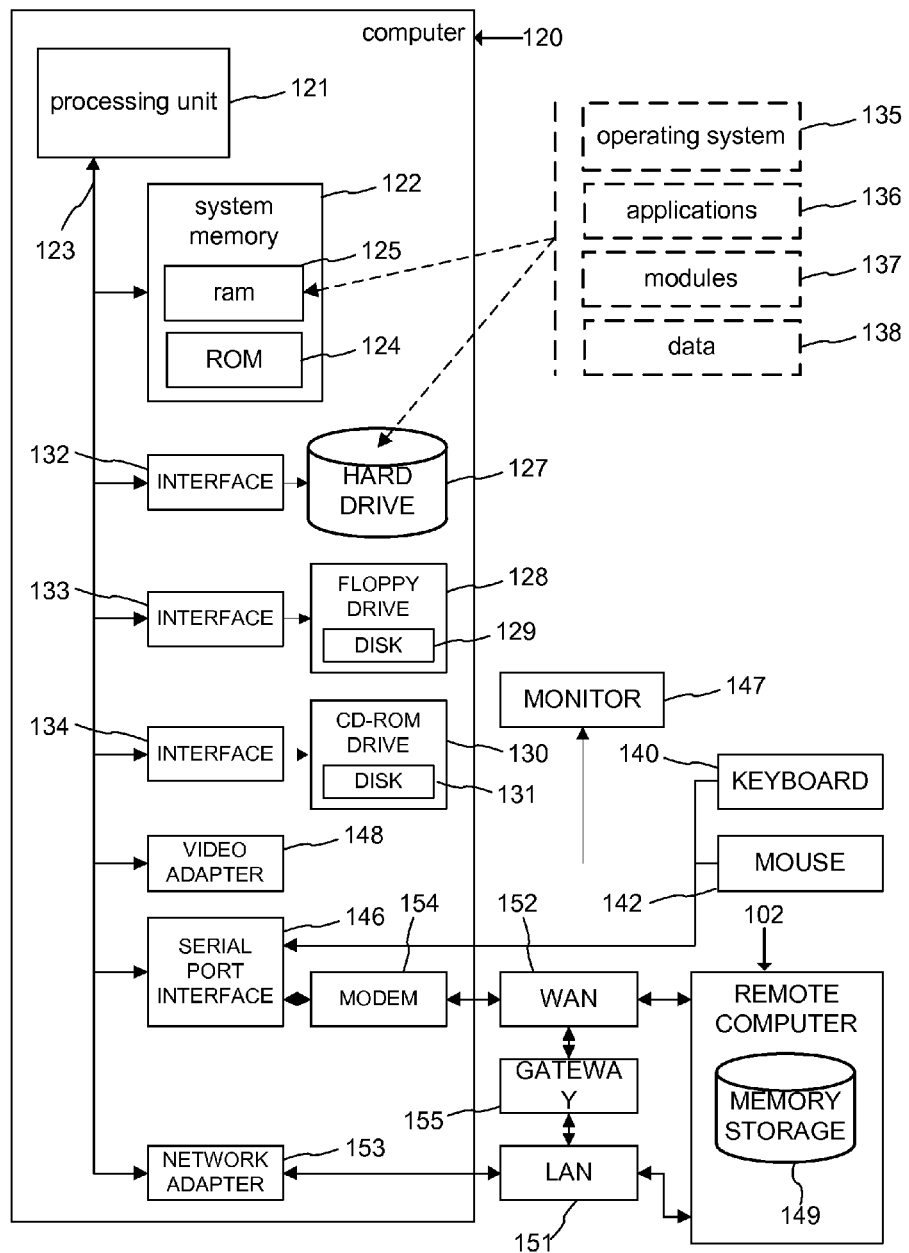
FIG. 6 is a block diagram of a computer system that can be used to implement aspects of the present disclosure.

FIG. 6 illustrates an exemplary computer system 120 that can serve as an operating environment for the software for use with the disclosed methods, for example as computer implemented methods. With reference to FIG. 6 an exemplary computer system for implementing the disclosed method includes a computer 120 (such as a personal computer, laptop, palmtop, set-top, server, mainframe, hand held device, and other varieties of computer), including a processing unit 121, a system memory 122, and a system bus 123 that couples various system components including the system memory to the processing unit 121. The processing unit can be any of various commercially available processors, including INTEL® x86, PENTIUM® and compatible microprocessors from INTEL® and others, including Cyrix, AMD and Nexgen; Alpha from Digital; MIPS from MIPS Technology, NEC, IDT®, Siemens, and others; and the PowerPC from IBM® and Motorola. Dual microprocessors and other multiprocessor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. A basic input/output system (BIOS), containing the basic routines that help to transfer information between elements within the computer 120, such as during start-up, is stored in ROM 124. The system memory includes read only memory (ROM) 124 and random access memory (RAM) 125.

The computer 120 may further include a hard disk drive 127, a magnetic disk drive 128, for example to read from or write to a removable disk 129, and an optical disk drive 130, for example to read a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer readable media provide nonvolatile storage of data, data structures (databases), computer executable instructions, etc. for the computer 120. Although the description of computer readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A user can enter commands and information into the computer 120 using various input devises, such as a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 6. The logical connections depicted in FIG. 6 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (for example via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device. It will be appreciated that the network connections shown are exemplary and other means of establishing a communications link between the computer systems (including an Ethernet card, ISDN terminal adapter, ADSL modem, 10BaseT adapter, 100BaseT adapter, ATM adapter, or the like) can be used.

The methods, including the acts and operations they comprise, described above can be performed by the computer 120. Such acts and operations are sometimes referred to as being computer executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

Figure 7:
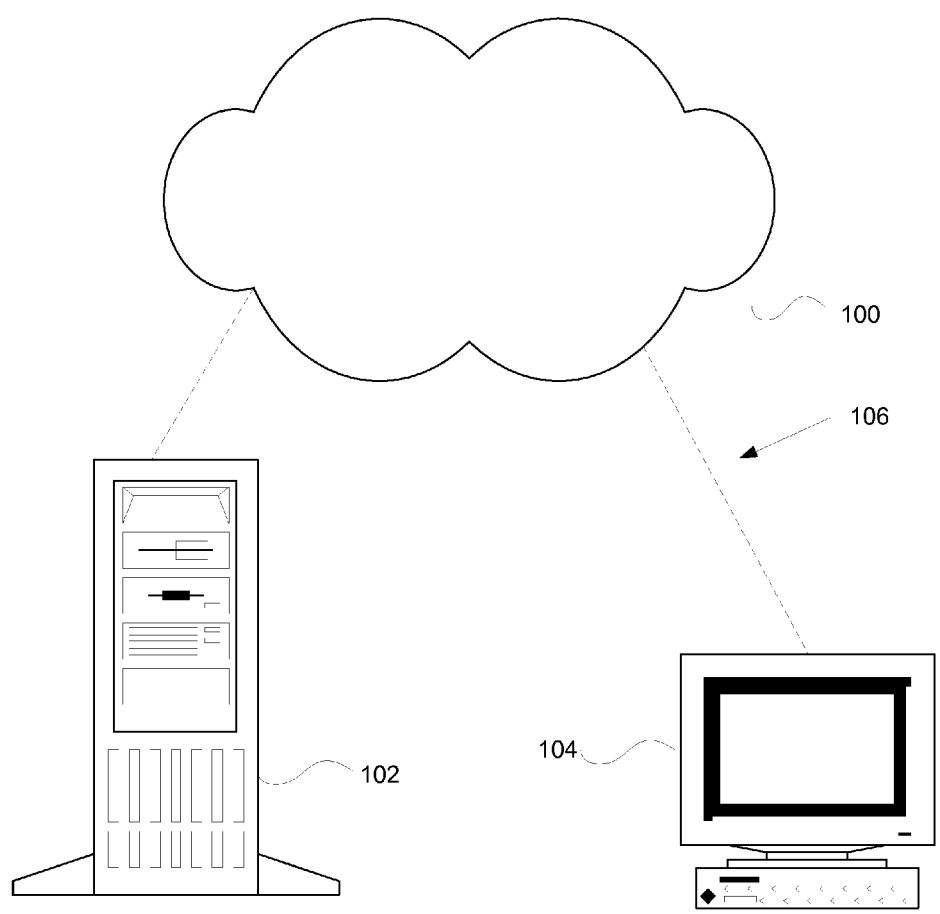
FIG. 7 is a diagram of a distributed computing environment in which aspects of the present disclosure can be implemented.

FIG. 7 illustrates a distributed computing environment in which the software and/or database elements used to implement the methods and systems of the present disclosure may reside. The distributed computing environment 100 includes two computer systems 102, 104 connected by a connection medium 106, although the disclosed method is equally applicable to an arbitrary, larger number of computer systems connected by the connection medium 106. The computer systems 102, 104 can be any of several types of computer system configurations, including personal computers, multiprocessor systems, handheld devices, and the like. In terms of logical relation with other computer systems, a computer system can be a client, a server, a router, a peer device, or other common network node. Additional computer systems 102 or 104 may be connected by an arbitrary number of connection mediums 106. The connection medium 106 can comprise any local area network (LAN), wide area network (WAN), or other computer network, including but not limited to Ethernets, enterprise-wide computer networks, intranets and the Internet.

Portions of the software for determining food product origin as well as databases storing the isotopic and trace element correlation data can be implemented in a single computer system 102 or 104, with the application later distributed to other computer systems 102, 104 in the distributed computing environment 100. Portions of the software for determining food product origin may also be practiced in a distributed computing environment 100 where tasks are performed by a single computer system 102 or 104 acting as a remote processing device that is accessed through a communications network, with the distributed application later distributed to other computer systems in the distributed computing environment 100. In a networked environment, program modules comprising the software for determining food product origin as well as databases storing the isotopic and trace element correlation data can be located on more than one computer system 102 or 104. Communication between the computer systems in the distributed computing network may advantageously include encryption of the communicated data.

The disclosure is illustrated by the following non-limiting Examples.

EXAMPLES

Example 1

This study examines the response to citalopram through a re-analysis of the data available from National Institute of Mental Health (NIMH): the Sequenced Treatment Alternatives to Relieve Depression (STAR*D) database. NIMH provided a public release of the STAR*D database in August of 2008. The design of the STAR*D study has been described elsewhere (Fava et al., *Psychiatr Clin North Am* (2003): 26:457-494). The STAR*D project enrolled more than 4,200 outpatients (ages 18-75) diagnosed with non-psychotic major depressive disorders. Data were collected from 41 primary care and mental health clinics. All of these patients were prescribed citalopram. If patients did not achieve remission or could not tolerate the medication, they were encouraged to proceed to the next random assignment, where they tried other medications or cognitive therapy. Those who achieved remission or reduction in symptoms and tolerated acute treatment were followed for 12-months.

Genetic profiles were available on 1,933 cases within the STAR*D database. The DNA sampling and the definition of remission have been described in a previous publication. Briefly, patients were considered responsive to treatment if at follow-up they were in remission; defined as patients scoring 5 or less on the Quick Inventory of Depressive Symptomatology (Clinician Rating) at follow-up. Genotyping was conducted on two platforms, Affymetrix Human Mapping 500K Array Set and the Affymetrix Genome-Wide Human SNP Array 5.0. This resulted in 430,198 validated Single Nuclide Polymorphism (SNP) for each case. Garriock et al. identified the top 25 SNPs associated with response to citalopram in a Genome Wide Association Study (Garriock et al., *Biol Psychiatry* (2010): 67(2):133-8). This study focused on these 25 markers because they were the most likely SNPs that might affect response.

Figure 4:
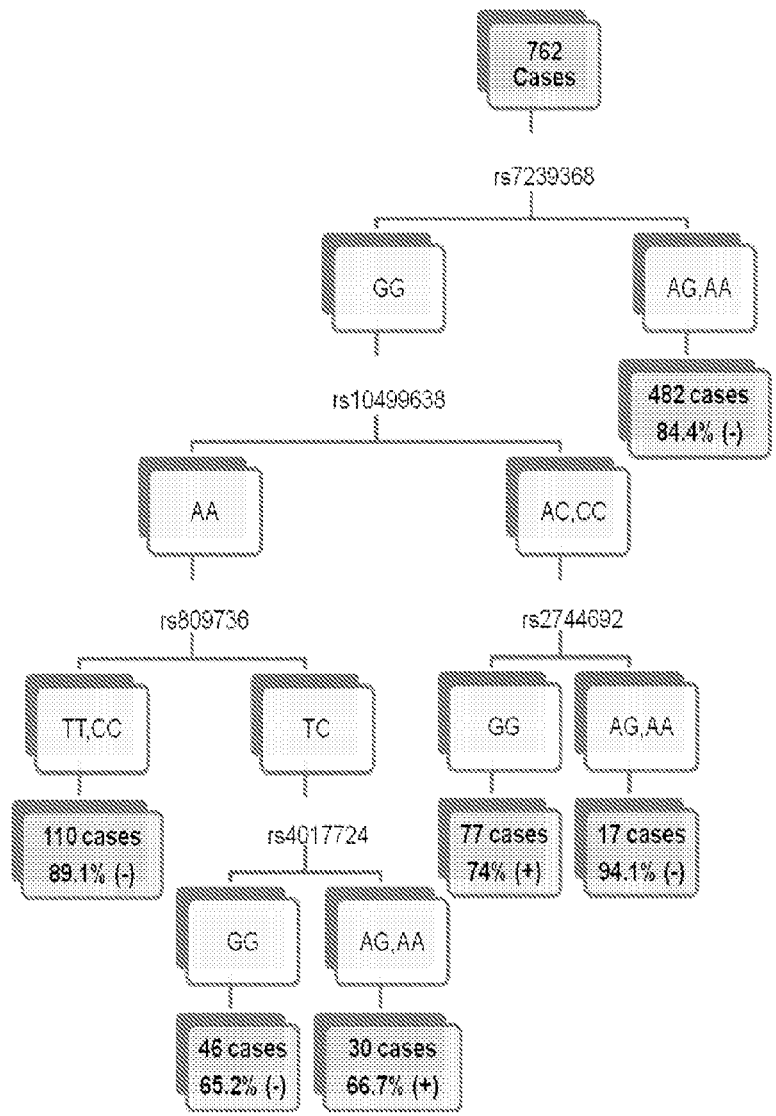
FIG. 4 shows the classification of response to citalopram for 762 case for the first of three boosted trees. (+) indicates positive and (−) indicates negative response to citalopram.

The classification of cases within the STAR*D database into different subgroups was done using CART procedure within Statistical Package for the Social Sciences (SPSS). CART classifies cases within the data set by progressively splitting the data to into two additional classes (two child nodes) so that the new classes can explain the most variance of the response to citalopram. In particular, at every step, the CART procedure used the Gini index (quadratic entropy), to select one of the 25 SNPs to classify the cases within the database. The procedure continued until all cases were classified into subgroups of at least 10 cases. The CART procedure leads to a classification tree (for an example see FIG. 4). Each node along a branch in the tree describes the presence of a specific genetic marker. The entire branch describes a particular genetic profile. The final node in the branch shows the subgroup of patients with same genetic profile and, as far as possible, homogenous response to citalopram. For example, the right hand branch of the tree in FIG. 4 describes the situation where rs7239368 is AG or AA. A total of 482 patients fall into this branch, and 84.4% of these patients respond negatively to citalopram. Therefore, if the patient-at-hand has this genetic profile that matches this group, then there is a good chance that this patient will also respond negatively to citalopram.

In boosted trees, the analyst selects misclassified cases and fits a separate tree to these cases. The procedure is repeated hundreds of times and the weighted average of the ensemble of trees is used to make the final predictions. Studies have shown that boosted trees are more accurate than other classification systems such as logistic regression or trees without boosting; but boosted trees are difficult to interpret. A variant of boosted trees was developed, where the branches of the tree lead to subgroups where the probability of positive or negative response to citalopram is significantly different from 0.5 (p-value≤0.10). This approach does not classify all cases, but the cases it does classify fall into categories where the probability of response is significantly different from 0.5. The algorithm used was as follows:

1. Fit a CART (10 fold cross-validation and pruning factor of 1) to all unclassified cases and identify the subgroups classified by each branch in the tree.
2. Stop if none of the subgroups identified have a probability of positive or negative response significantly different from 0.05 (p-value≤0.10).
3. Re-name cases within subgroups with probability of positive or negative response not significantly different from 0.5 (p-value>0.10) to "Unclassified cases." Specify exclusion rules by using the branches that defined the subgroups that were re-named.
4. Apply CART (10 fold cross-validation and pruning factor of 1) to cases not excluded in the previous step. This results in a new tree. The branches within this tree specify the inclusion rules.
5. Go to step one.

This procedure leads to an ensemble of trees. Each tree predicts the response for a particular set of cases. The last tree contains cases from subgroups, where none meet the significance criterion. This procedure improves the performance of the initial tree like other boosting method. Unlike other boosting procedures, it has the advantage that it stops after a few iterations and is easily interpretable as every branch within each of the ensemble of trees provides a rule for defining a specific subgroup of cases. Additional detail on the boosting procedure is available through the first two authors.

The CART procedure was applied with 10-fold cross-validation and pruning, therefore the percent of cases correctly classified was unlikely to be due to over-fitting. The results present are data on the accuracy of the cross-validated trees.

Results

The initial CART (without boosting) yielded a tree that correctly predicted 56% of cases (standard error in risk 0.01). One could accurately predict 60% of cases by merely predicting no one would benefit from citalopram. Therefore, the initial performance of CART was not adequate; thus a boosting procedure was used to identify subset of patients for whom response to citalopram could be more accurately predicted. The initial tree provided 71 subgroups of patients (branches in the tree), each with a different probability of positive response to citalopram. Subgroups of patients were excluded, where the probability of positive or negative response was not significantly different from random tossup.

The CART analysis algorithm was then repeated for these more homogenous subgroups, as per algorithm provided earlier.

Figure 5:
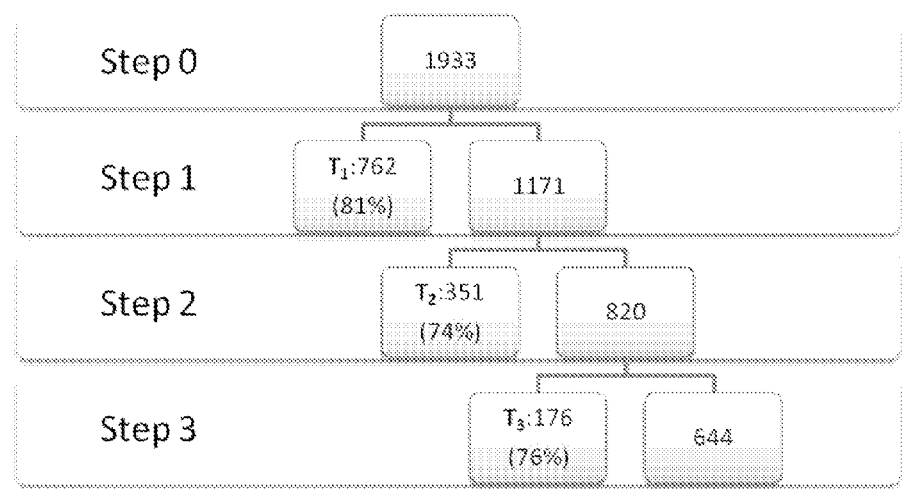
FIG. 5 shows the accuracy of predictions in different related trees T1, T2 and T3.

The boosted CART procedure created an ensemble of 3 related trees, as shown in FIG. 5. In step 0, there were 1933 cases. The first boosted tree was organized for 762 cases and accurately predicted 81% of these cases in cross-validation. In step 2, a tree was organized for 351 cases and accurately predicted 74% of these cases in cross validation. In steps 3, a tree was organized that accurately predicted 76% of 176 cases. This algorithm left 644 cases (33%) of cases as unclassified; on these cases the algorithm makes no predictions.

Table 2 provides 91 rules for identifying which one of the 3 trees are appropriate. These rules were derived from branches excluded from the analysis and are refered to as exclusion rules. In cases where none of the 3 trees are appropriate, a prediction was not made. Once a tree has been selected, then each branch within the tree identifies a unique subgroup of patients, these rules are referred to as the inclusion rules. There were 16 inclusion rules, see Table 1. These rules can be used to further classify the patient into relevant subgroups. Once a patient has been classified into a relevant sub-group, then the experience of the group can be used to predict the outcome for the patient.

Table 1 identifies 16 inclusion rules identifying subgroups with different probability of positive response to citalopram, ranging from 84% to 6% (94% probability of negative response). The number of cases that fall within each subgroup is different, ranging from 13 to 482 cases. A patient may have more confidence in the advice of the system when they fall in the larger groups or if they fall in a subgroup with more extreme probability of positive/negative response. A statistical test can be done for the individual patient to see if the probability of positive response within their subgroup is significantly different from a particular value, say 0.5. Such a test provides guidance only to the patients that fall within the subgroup.

The overall accuracy of the ensemble of the 3 trees is the sum of the accuracy of each one, weighted by the percent of cases classified by the trees. Therefore, the ensemble as a whole makes no predictions on 644 cases (33% of cases) and correctly classifies 78% of the remaining 1289 cases (67% of cases).

Discussion

These data indicates that for ⅔ of patients the methods disclosed herein can accurately predict response to citalopram. Not only were the predictions statistically significant but the effect size was large. The Appendix includes 91 rules that were used in deciding which tree is relevant and 16 rules for identifying the subgroup within a tree. These rules indicate different genetic markers in different sets of cases.

The existence of so many different rules suggests that, within the central nervous system, there may be multiple physical processes that lead to depression. Depression is not a single disease; there are many variants of depression and it may be possible that the rules in Table 2 correspond to variations in types of depression. Amongst the combinations of alleles at different genes comprising the subgroups in Table 1, two notable ones were observed. These were characterized by the prediction of either success or failure in relatively large groups of patients, as well as a possibility of biological interaction, in addition to their observed statistical interaction. Of the three markers identifying 110 cases with an 89% chance of non-response listed above, rs7238368 and rs809736 occur in the genes nucleolar protein 4 (NOL4), and RAR-related orphan receptor A isoform a (RORA), respectively, while rs10499638 is intergenic. NOL4 is highly expressed in both brain and testis. Its function is poorly understood. Nucleoli are the sites of ribosome-subunit production, although they are increasingly thought to have a variety of other functions. Furthermore, nucleolar dysfunction may be related to disease etiology, including in neuropsychiatric conditions such as Alzheimer's. RORA belongs to the NR1 subfamily of nuclear hormone receptors. It may be involved in neuro-protection and cerebellar development, and is a recent candidate gene for autism. Abnormalities in neuro-endocrine systems (of which hormone receptors are a component), particularly in the Hypothalamic-Pituitary-Adrenal Axis, have long been associated with depression.

Another subgroup was defined by markers in rs2697992, which occurs in retinoblastoma protein-binding zinc finger (PRDM2), rs6127921, which is about 106 kb downstream of bone morphogenetic protein 7 precursor (BMP7), along with rs6046805, which occurs in the open reading frame C20orf26. This subgroup consisted of 128 subjects and had a 69% probability of response. PRDM2 binds to RIZ, a zinc-finger protein which regulates transcription during neuronal differentiation. BMP7 has neuroprotective properties and can induce oligodendroglial and astrocytic differentiation, thus impairing neuronal migration. These two proteins are therefore involved in the development of cell types in neural tissue whose differentiation is mutually antagonistic, lending face validity to a biological interaction at either the protein or systems level.

TABLE 1

Inclusion Rules for Defining Subgroups within the 3 Trees

| Tree | Node | rs2744692 | rs2697992 | rs4017724 | rs6817919 | rs10499638 | rs809736 | rs7239368 |
|---|---|---|---|---|---|---|---|---|
| T1 | 2 | | | | | | | AG |
| | | | | | | | | AA |
| T1 | 5 | | | | | AA | TT | GG |
| | | | | | | | CC | |
| T1 | 7 | GG | | | | AC | | GG |
| | | | | | | CC | | |
| T1 | 8 | AG | | | | AC | | GG |
| | | AA | | | | CC | | |
| T1 | 9 | | | | GG | AA | TC | GG |
| T1 | 10 | | | | AG | AA | TC | GG |
| | | | | | AA | | | |
| T2 | 4 | | | GG | | | | |
| | | | | CC | | | | |
| T2 | 7 | | | CG | | | | |
| T2 | 8 | | | CG | | | | |

TABLE 1-continued

Inclusion Rules for Defining Subgroups within the 3 Trees

| Tree | Node | | | | | | |
|---|---|---|---|---|---|---|---|
| T2 | 9 | GG | | | TTT C | | |
| T2 | 10 | GG | | | CC | | |
| T2 | 11 | CG CC | | | | | |
| T2 | 12 | CG CC | | | | | |
| T3 | 1 | | | TT | | | |
| T3 | 3 | | | TC | | | AA |
| T3 | 4 | | | TC | | | AG GG |

| Tree | Node | rs6046805 | rs6127921 | rs11701162 | Prediction | P(%) | N |
|---|---|---|---|---|---|---|---|
| T1 | 2 | | | | F | 84 | 482 |
| T1 | 5 | | | | F | 89 | 110 |
| T1 | 7 | | | | S | 74 | 77 |
| T1 | 8 | | | | F | 94 | 17 |
| T1 | 9 | | | | F | 65 | 46 |
| T1 | 10 | | | | S | 67 | 30 |
| T2 | 4 | TT | | | S | 84 | 62 |
| T2 | 7 | TT | | TG | S | 77 | 13 |
| T2 | 8 | TT | | TT GG | F | 79 | 14 |
| T2 | 9 | TC CC | | | F | 90 | 81 |
| T2 | 10 | TC CC | | | S | 69 | 13 |
| T2 | 11 | TC CC | AA | | S | 69 | 128 |
| T2 | 12 | TC CC | AC CC | | F | 65 | 40 |
| T3 | 1 | | | | F | 86 | 76 |
| T3 | 3 | | | | F | 71 | 14 |
| T3 | 4 | | | | S | 70 | 86 |

TABLE 2

| Tree | Node | rs2744692 | rs2697992 | rs4654712 | rs1437956 | rs11128623 | rs1858385 | rs4017724 | rs9879204 | rs6817919 | rs10518306 | rs17151283 | rs788725 | rs10499638 | rs17172738 | rs6966038 |
|---|---|---|---|---|---|---|---|---|---|---|---|---|---|---|---|---|
| T1 | | | | | | AG | | | TC | | | | | | | AG |
| T1 | | | | | | AG | | AG | TT | | | | | | | GG |
| T1 | | | | | | AA | | | CC | | | | | | | |
| T1 | | | | | | GG | | | | | | | | | | |
| T1 | | CG | | TT | | AA | AA | | | | | | | | | |
| T1 | | CC | | | | GG | | | | | | | | | | |
| T1 | | GG | | | | AA | | | | | | | | | | |
| T1 | | | | AT | | AA | GG | GG | | | | | | | | |
| T1 | | | | TT | | GG | AG | | | | | | | | | |
| T1 | | GG | | | TT | AA | | GG | | | | | GG | | | AA |
| T1 | | | | | | GG | AA | | TC | | | | | AC | | |
| T1 | | GG | | | | AA | | | | | | | | CC | | |
| T1 | | GG | | | | GG | | | | | GG | | | | | AG |
| T1 | | | | | | AA | | | | | | | | AA | | GG |
| T1 | | | | | | GG | | | | | | | | | | |
| T1 | | | | | | AA | | AG | | | | AA | | | | AA |
| T1 | | | | | | GG | | AA | | | | GG | | | | |
| T1 | | | | | | AA | | AG | | GG | | | | | | |
| T1 | | | | | AA | GG | | | | | | | | | | |
| T1 | | | | | AT | AA | | GG | | | | AG | | AC | | AA |
| T1 | | | | | AA | GG | | AG | | | | AA | | CC | | |
| T1 | | | | | TT | AA | | AA | | | | GG | | | | |
| T1 | | | | | AA | GG | | | | | TTC | | | | | |
| T1 | | | | | AT | AA | | | | | C | | | | | |
| T1 | | | | | AA | GG | | | | | CC | | | | | |
| T1 | | | | | AT | AA | | | | | | AA | CC | AC | | AG |
| T1 | | | | | AA | GG | | | | | | GG | | CC | | GG |
| T1 | | | | | AT | AA | | | | | | | | | | |
| T1 | | | | | AA | GG | | | | | | | | | | |
| T1 | | | | | AT | AA | | | | | | | | | | AA |
| T1 | | | | | AA | GG | | | | | | | AC | | | |
| T1 | | | | | GG | AA | GG | | TTT | | | | | | | |
| T1 | | | | | AG | GG | AG | | C | | | | | | | |
| T1 | | | | | GG | AA | GG | | TTT | | | | | | | |
| T1 | | | | | AG | GG | AG | | C | | | | | | | |
| T1 | | | | | | AA | | | TTT | | | AA | AC | | GG | AG |
| T1 | | | | | | GG | | | C | | | GG | CC | | CG | GG |
| T1 | | | | | | AA | | | | | | | | | CC | AA |
| T1 | | | | | | GG | | | | | | | AA | | GG | |
| T1 | | | | | | AA | | | | | | | | | GG | AA |
| T1 | | | | | | GG | | | | | | AG | | | CG | |
| T1 | | | | | | AA | | | | | | AA | | | GG | AA |
| T1 | | | | | | GG | | | | | | | | | CG | |
| T1 | | | | | | AA | | | | | | | | | AA | AG |
| T1 | | | | | | GG | | | | | | | | | AA | GG |
| T1 | | AT | | TT | | AA | | | | | CC | | | | GG | AA |
| T1 | | | | AT | | GG | | | | | TC | AG | | | | |

Show the exclusion rules for the tree 1 through 3:

TABLE 2-continued

The exclusion rules for tree 2 are as follows:

| | | | | | | | | | |
|---|---|---|---|---|---|---|---|---|---|
| T1 | | | CG/CC | | AA | GG | | | GG |
| T1 | | | | | | | CC/TT | AA/GG | AG/GG |
| T2 | AA/GG/AG | | | | | | | | AG |
| T2 | AA/GG/AG | | CC/GG/CG | AA | | | | | |
| T2 | AA/GG/AG | | | AT/TT/AA | | | | | |
| T2 | AA/GG/AG | | | AT/TT/AA | | | AG | | |
| T2 | AA/GG/AG | | | AT/TT/AA | | AA/GG/AA | | | |
| T2 | AA/GG/AG | | | AT/TT/AA | AA/TT | | | | |
| T2 | AG | | | AT/TT/AA | AA | GG | TC | AG | |
| T2 | | | | AT/TT | | | TC | | AC |
| T2 | | | | AT/TT/AA | | | TT | | AA/CC |
| T2 | | | | AT/TT/AA | | | GG | AG/GG/AG | |
| T2 | | | CG/GG/CC/GG/CG/CC | AT/TT | | | | AG/GG | AA |
| T2 | | | GG/CC/CG/GG/CC/CG | AT/TT/AT | | AA/GG/AA/GG | AG/AA/GG | | AA/CC/AC |
| T2 | | | CG/CC/GG/CC/CG/CC | AT/TT/AT | | | TTC/C | | |
| T2 | | | | TT/AA/TT/AA | | | | | |
| T2 | | | | | | | | GG | CC |
| T2 | | | | | | | | AA/AG | AA/AG/AA/AG |

TABLE 2-continued

The exclusion rules for tree 3 were as follows:

| | | | | | | | | | | |
|---|---|---|---|---|---|---|---|---|---|---|
| T3 | GG | | | | | | | | | |
| T3 | | TT | | | | | | | | |
| T3 | | | AA TT AA TT | | | | | | | |
| T3 | | | | | | | CC | AG | | |
| T3 | AA GG | AA TT AT | AT | | | | | AG | | |
| T3 | | AA | AA | | | | | AA GG | | |
| T3 | AA GG | AA TT AT | AT TT | | | | | | | |
| T3 | | AA | | | TC | | | | | |
| T3 | | TT | TT | | | | | | | |
| T3 | | AT | | | | | | GG | | |
| T3 | AG AA | AT | | AA | | | | | AC | |
| T3 | AA GG | AT | TT | AA | | AG | | | | |
| T3 | GG | AT | AT AA | | | | | | | CG |
| T3 | GG GG AG AA AA GG AG AA | AA TT | AA | | | | | | | CC | GG AA |
| T3 | | AT | | | | | | | AA | AG |
| T3 | | AA TT | | | | | | | | AG GG AA |
| T3 | | AA TT | AA | | | | | | | AA |
| T3 | GG | | | | | | | | | CG | AA |
| T3 | | | | | TC | | | | | CC | AA |
| T3 | | | | | | | | | | CG CG CG CC |
| T3 | | | | | | | | | | |

TABLE 2-continued

Show the exclusion rules for the tree 1 through 3:

| Tree | Node | rs2368416 | rs4146387 | rs201371 | rs12883508 | rs809736 | rs439783 | rs7239368 | rs6046805 | rs6127921 | rs11701162 | Pred | P(%) | N |
|---|---|---|---|---|---|---|---|---|---|---|---|---|---|---|
| T1 | | | | | | | | GG | | | | Not in T1 | | |
| T1 | | | | | | | | GG | | | | Not in T1 | | |
| T1 | | | | | | | | AG | | | TG | Not in T1 | | |
| T1 | | | | | | | | AA | | | TT | Not in T1 | | |
| T1 | | | | CG | | | | AG | | | TG | Not in T1 | | |
| T1 | | | | | | | | AA | | | TT | Not in T1 | | |
| T1 | | AA | | | | | | GG | | | TG | Not in T1 | | |
| T1 | | AG | | | | | | AG | | | TT | Not in T1 | | |
| T1 | | | | | | | | AA | | | GG | Not in T1 | | |
| T1 | | GG | | | | TT | | AG | | | | Not in T1 | | |
| T1 | | | | | | | | AA | | | | Not in T1 | | |
| T1 | | | | | | | AA | GG | | AA | | Not in T1 | | |
| T1 | | | | | | | | GG | | AC | | Not in T1 | | |
| T1 | | | | | | | | GG | | AC | | Not in T1 | | |
| T1 | | GG | | | | | | AG | | CC | | Not in T1 | | |
| T1 | | | | | | | AA | AA | | AC | | Not in T1 | | |
| T1 | | | | | | | GG | GG | | CC | | Not in T1 | | |
| T1 | | | | | | | | AG | | AA | GG | Not in T1 | | |
| T1 | | AA | | CG | | | AG | AA | | AA | GG | Not in T1 | | |
| T1 | | AG | | GG | | | AA | GG | | | | Not in T1 | | |
| T1 | | | | | | TT | AG | AG | | AA | GG | Not in T1 | | |
| T1 | | | | | | | AA | AA | | | | Not in T1 | | |
| T1 | | | | | | | AG | GG | | AA | GG | Not in T1 | | |
| T1 | | | | | | TC | AA | AG | | | | Not in T1 | | |
| T1 | | | | | | | | AA | | | | Not in T1 | | |
| T1 | | | | | | | AG | AG | | AA | GG | Not in T1 | | |
| T1 | | | | | | | AA | AA | | | | Not in T1 | | |
| T1 | | | | | | TT | AA | AG | | AA | GG | Not in T1 | | |
| T1 | | | | | | | AG | AA | | | | Not in T1 | | |
| T1 | | | | | | | AA | GG | | AC | | Not in T1 | | |
| T1 | | | | | | | GG | AG | | CC | | Not in T1 | | |
| T1 | | | | | | | | AA | | AA | GG | Not in T1 | | |
| T1 | | | | | | | | GG | | | TT | Not in T1 | | |

TABLE 2-continued

The exclusion rules for tree 2 are as follows:

| | | | | | | | |
|---|---|---|---|---|---|---|---|
| T2 | | GG | | | TT | | Not in T2 |
| T2 | | | | | TC | | Not in T2 |
| T2 | | | | | CC | | Not in T2 |
| T2 | | GG | | | TT | | Not in T2 |
| T2 | | GG | | | TT | | Not in T2 |
| T2 | | GG | | | TC | | Not in T2 |
| T2 | | GG | | | CC | | Not in T2 |
| T2 | AG | GG | | | TC | | Not in T2 |
| T2 | GG | GG | | | CC | | Not in T2 |
| T2 | | GG | | | TC | | Not in T2 |
| T2 | | GG | | | CC | | Not in T2 |
| T2 | | GG | TT | | TC | | Not in T2 |
| T2 | | GG | TC | | CC | | Not in T2 |
| T2 | AG | GG | | AG | TC | | Not in T2 |
| T2 | GG | GG | | AA | CC | | Not in T2 |
| T2 | | GG | | AA | TC | AA | Not in T2 |
| T2 | | GG | | | CC | | Not in T2 |
| T2 | AA | GG | | | TC | | Not in T2 |
| T2 | AG | GG | | | CC | AA | Not in T2 |
| T2 | GG | GG | | | TC | | Not in T2 |
| T2 | AA | AG | | | CC | | Not in T2 |
| T2 | | | TT | | TC | | Not in T2 |
| T2 | | GG | TC | | CC | | Not in T2 |
| T2 | | GG | TT | | TC | | Not in T2 |
| T2 | | | TC | | CC | | Not in T2 |
| T2 | | | | | TC | AA | Not in T2 |
| T2 | | | | | CC | AA | Not in T2 |
| T2 | | | | | TC | AA | TG | Not in T2 |
| T2 | GG | | | | CC | AA | TT | Not in T2 |
| T2 | | | | | | | GG | Not in T2 |

The exclusion rules for tree 3 were as follows:

| | | | | | |
|---|---|---|---|---|---|
| T3 | AG | GG | | | AA | Not in T3 |
| T3 | AA | GG | | | AC | Not in T3 |
| T3 | GG | AG | | | CC | Not in T3 |
| | | | | | AC | |
| | | | | | CC | |
| T3 | | | | | | Not in T3 |

TABLE 2-continued

| | | | | | | | | | |
|---|---|---|---|---|---|---|---|---|---|
| T3 | AA | | | | | | | | Not in T3 |
| T3 | GG | GG | | | | | | | Not in T3 |
| T3 | AG | GG | | | | | | | Not in T3 |
| T3 | | | CG | | | | AC | | Not in T3 |
| T3 | | | CC | | | | CC | | Not in T3 |
| T3 | | | CG | | | | AC | | Not in T3 |
| T3 | | | CC | | | | CC | | Not in T3 |
| T3 | | | | | AG | | AA | | Not in T3 |
| T3 | | | | | | | AC | | Not in T3 |
| T3 | | | CG | | AG | | AC | | Not in T3 |
| T3 | | | CC | | AA | | AA | | Not in T3 |
| T3 | | | CG | | | | AC | | Not in T3 |
| T3 | | | CC | | | | AA | | Not in T3 |
| T3 | AG | | | AG | GG | | AC | | Not in T3 |
| T3 | | | | AA | AA | | AA | | Not in T3 |
| T3 | | | | AG | GG | | AC | | Not in T3 |
| T3 | | | | AA | AA | | AC | | Not in T3 |
| T3 | | | | TT | | | AA | | Not in T3 |
| T3 | | | | TC | | | AC | | Not in T3 |
| T3 | | | | TT | | | AC | | Not in T3 |
| T3 | | | | TC | | | AC | | Not in T3 |
| T3 | | | | TT | | | | | Not in T3 |
| T3 | | | | TC | | | | | Not in T3 |
| T3 | | | | TT | | | | | Not in T3 |
| T3 | | | | TC | | | | | Not in T3 |
| T3 | GG | | CC | | GG | | AA | GG | Not in T3 |
| T3 | AA | | | | AA | | AC | TT | Not in T3 |
| T3 | | | CG | | | CC | | | Not in T3 |
| T3 | | | GG | | | TC | | | Not in T3 |
| T3 | AG | | CC | | GG | | | | Not in T3 |
| T3 | | | | | AA | | | | Not in T3 |
| T3 | | | | | AG | | AC | | Not in T3 |
| T3 | | | | | GG | | AC | | Not in T3 |
| T3 | | | | | AG | | | | Not in T3 |
| T3 | | | | | | TT | | | Not in T3 |

Exclusion rules were used to decide which tree structure could be used to make predictions for a specific patient. If all 3 trees were excluded then no prediction could be made. Once a tree was selected, the inclusion rules were used to predict the outcome. The inclusion rules are provided in Table 1.

In view of the many possible embodiments to which the principles of the invention may be applied, it should be recognized that illustrated embodiments are only examples of the invention and should not be considered a limitation on the scope of the invention. Rather, the scope of the invention is defined by the following claims. I therefore claim as my invention all that comes within the scope and spirit of these claims.

I claim:

1. A method for predicting a subject's medical outcome, comprising:
    identifying a subject with a medical condition or at risk of acquiring a medical condition;
    predicting the subject's medical outcome by comparing the subject's genetic profile with a set of control genetic profiles, wherein the control genetic profiles are generated from a group of subjects with the same disease using classification and regression trees (CART) based on the presence of identifying genetic characteristics and wherein each node in a classification tree describes the presence of a specific genetic marker and each branch in the classification tree describes a genetic profile into one or more subgroups, wherein the one or more subgroups are classified based on similarity of medical outcome, and wherein matching a subject's genetic profile to a branch in the classification tree predicts the subject's medical outcome, wherein CART comprises a 10 fold cross-validation and pruning factor of 1 to all unclassified cases to classify the subgroups into the branches of the tree and CART is halted if none of the subgroups identified have a probability of positive or negative response of statistical significance, in which statistical significance is one in which a p-value is ≤0.10.

2. The method of claim 1, wherein CART is boosted.

3. The method of claim 1, wherein the method predicts medical outcome with at least 65% accuracy.

4. The method of claim 1, wherein the medical outcome is a disease progression.

5. A system for predicting a subject's medical outcome, comprising:
    identifying a group of subjects with the same disease;
    classifying the group of subjects with the same disease into one or more subgroups, wherein the one or more subgroups are classified based on similarity of medical outcome, using classification and regression trees (CART) to generate a classification tree based on the presence of identifying genetic characteristics and wherein each node in the classification tree describes the presence of a specific genetic marker and each branch in the classification tree describes a genetic profile that predicts a subject's medical outcome, wherein CART comprises a 10 fold cross-validation and pruning factor of 1 to all unclassified cases to classify the subgroups into the branches of the tree and wherein CART is halted if none of the subgroups identified have a probability of positive or negative response of statistical significance, in which statistical significance is one in which a p-value is ≤0.10.

6. The system of claim 5, wherein CART is boosted.

7. The system of claim 5, wherein the system predicts medical outcome with at least 65% accuracy.

8. The system of claim 5, wherein the medical outcome is response to citalopram.

9. A method for predicting a subject's medical outcome, comprising:
    identifying a subject with depression or at risk of acquiring depression;
    predicting the subject's medical outcome by comparing the subject's genetic profile with a set of control genetic profiles, wherein the control genetic profiles are generated from a group of subjects with depression using classification and regression trees (CART) based on the presence of identifying genetic characteristics, wherein each node in a classification tree describes the presence of a specific genetic marker and each branch in the classification tree describes a genetic profile into one or more subgroups, wherein the one or more subgroups are classified based on similarity of medical outcome in which medical outcome is response to administration of citalopram, wherein matching a subject's genetic profile to a branch in the classification tree predicts the subject's medical outcome and wherein the identifying genetic characteristics are the presence of single nucleotide polymorphisms (SNPs) rs7238368 and rs809736 in nucleolar protein 4 (NOL4) and rs10499638 in RAR-related orphan receptor A isoform a (RORA) indicating that the subject will not be responsive to citalopram or the identifying genetic characteristics are the presence of single nucleotide polymorphisms (SNPs) rs2697992 in retinoblastoma protein-binding zinc finger (PRDM2), rs6127921 in bone morphogenetic protein 7 precursor (BMP7), and rs604685 in open reading frame C20orf26 indicating that the subject will be responsive to citalopram.

* * * * *